US00PP21606P3

(12) United States Plant Patent
Barnsby

(10) Patent No.: US PP21,606 P3
(45) Date of Patent: Jan. 4, 2011

(54) APPLE TREE NAMED 'PLBAR B1'

(50) Latin Name: *Malus domestica*
Varietal Denomination: PLBAR B1

(75) Inventor: Dennis W. Barnsby, Pemberton (AU)

(73) Assignee: Teak Enterprises Pty Limited, Capel (AU)

( * ) Notice: Subject to any disclaimer, the term of this patent is extended or adjusted under 35 U.S.C. 154(b) by 41 days.

(21) Appl. No.: 12/214,790

(22) Filed: Jun. 20, 2008

(65) Prior Publication Data

US 2009/0055978 P1 Feb. 26, 2009

Related U.S. Application Data

(60) Provisional application No. 60/937,325, filed on Jun. 27, 2007.

(51) Int. Cl.
*A01H 5/00* (2006.01)

(52) U.S. Cl. ..... Plt./161

(58) Field of Classification Search ..... Plt./161, Plt./172

See application file for complete search history.

*Primary Examiner*—Kent L Bell
(74) *Attorney, Agent, or Firm*—Chris Svendsen

(57) ABSTRACT

'PLBAR B1' is a new apple tree that originated as a limb sport mutation of 'Cripps Pink.' The new variety is notable for its exceptional color and early maturity as compared to 'Cripps Pink.' Fruit of the new variety is mature and ready for harvest 14 to 18 days earlier than fruit of 'Cripps Pink.'

4 Drawing Sheets

Latin name of the genus and species of the plant claimed: *Malus domestica.*

Variety denomination: 'PLBAR B1'.

BACKGROUND AND SUMMARY OF THE VARIETY

'PLBAR B1' originated as a limb sport mutation of 'Cripps Pink' (U.S. Plant Pat. No. 7,880). It was discovered by the inventor in a cultivated orchard at Pemberton, Western Australia during the 1999-2000 growing season. 'PLBAR B1' was asexually propagated by field grafting during the 2001-2002 growing season at Pemberton, and has been shown to remain true to type over successive generations.

'PLBAR B1' is a new and distinct apple tree notable for its exceptional color and early maturity as compared to 'Cripps Pink.' Fruit of the new variety is mature and ready for harvest about 14 to 18 days earlier than fruit of 'Cripps Pink,' as measured by a difference of 2 to 3 points in the industry standard starch score range of 1 to 6.

BRIEF DESCRIPTION OF THE PHOTOGRAPHS

DETAILED BOTANICAL DESCRIPTION OF THE VARIETY

Figure 1:
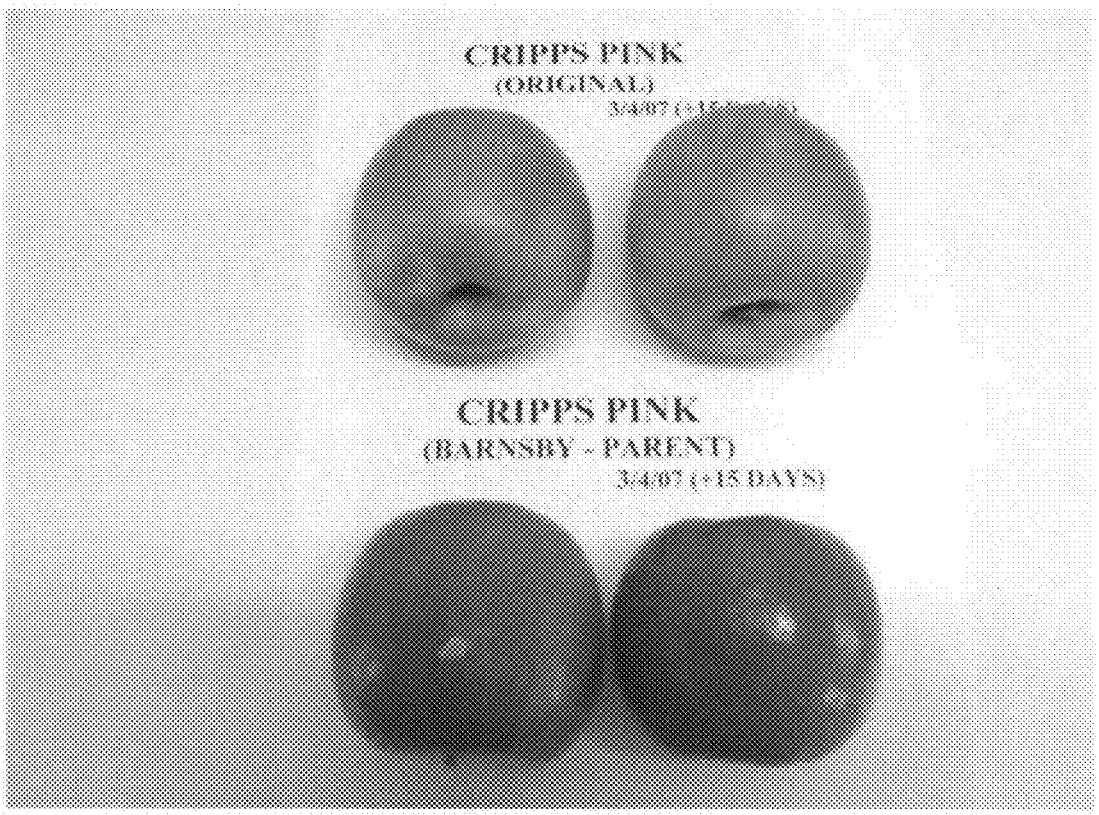
FIG. 1 shows the fruit of 'PLBAR B1'.
Figure 2:
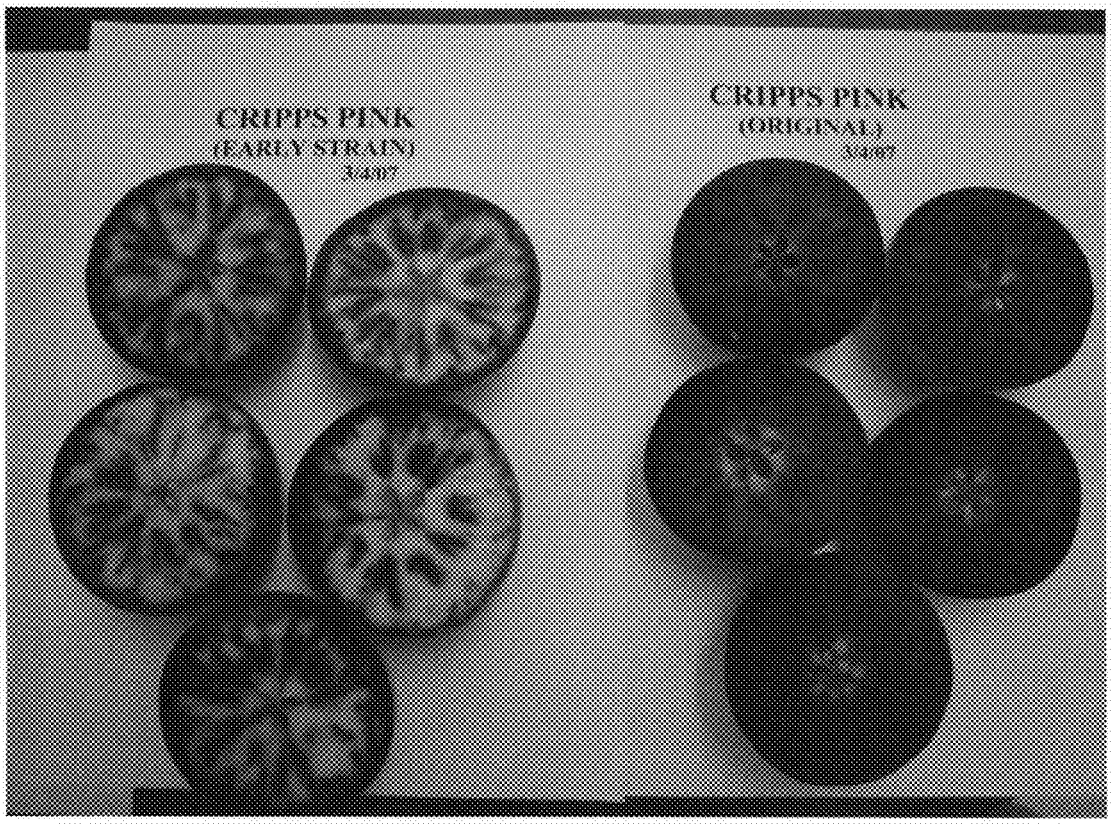
FIG. 2 shows a comparison of the fruit of 'PLBAR B1' (on the left) to parent variety 'Cripps Pink' (on the right) after starch testing.
Figure 3:
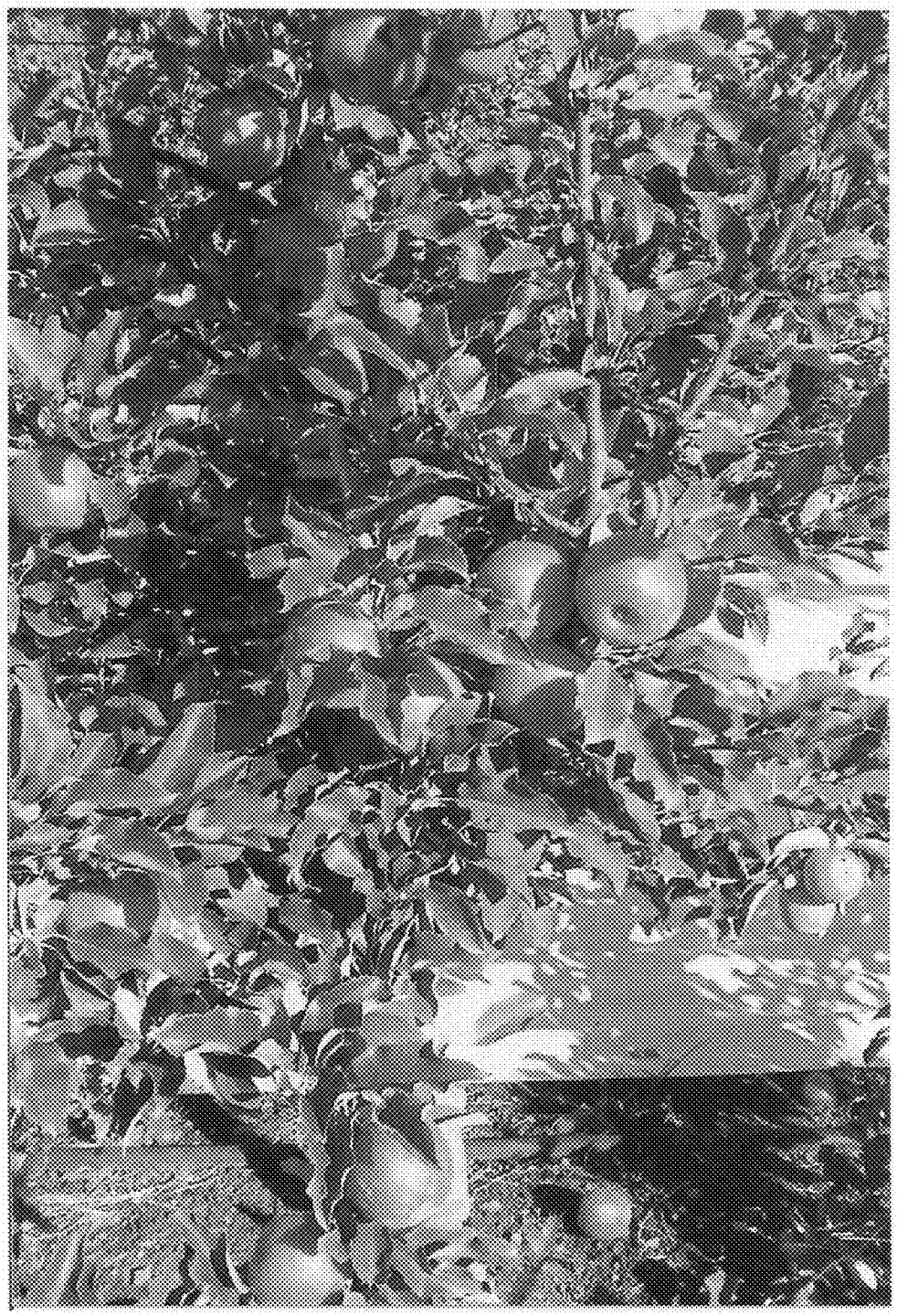
FIGS. 3 and 4 show a tree of the 'PLBAR B1' variety.
Figure 4:
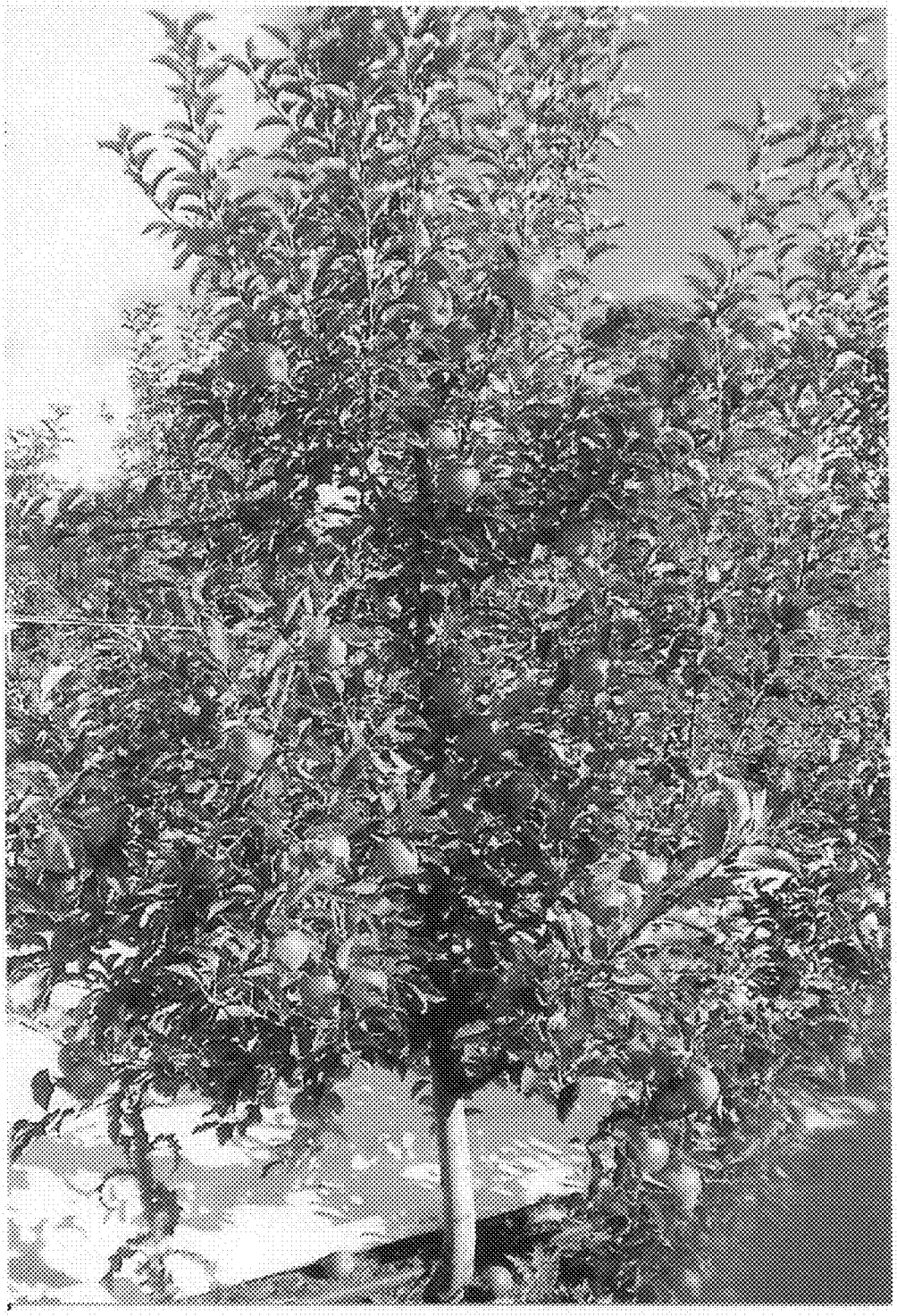

The following detailed botanical description is based on observations of first generation trees planted in 2003, and described during the 2006-2007 and 2007-2008 growing seasons at Pemberton, Western Australia. Color descriptions refer to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Medium to large with dense foliage, upright habit; Very vigorous; Height 3.1 to 4.1 m; Spread 1.75 to 2 m.

Trunk: Medium stocky, diameter 23 cm to 25 cm at 30 cm above graft union; Bark smooth, color Grey-Brown RHS 199A.

*Lenticels.*—Medium density, approximately 10-12 per square centimeter, White RHS 155B in color, length 0.12 mm, diameter 0.08 mm, typical of 'Cripps Pink.'

Branches: Thick, smooth, upright.

*Branching habit.*—Much branched with average branching angles (inside measurement) of 45 degrees to 50 degrees relative to the tree trunk if allowed to grow naturally; Length 47-65 cm on one year old shoot; Width 6 mm.

*Color.*—Grey-brown RHS 199B.

*Shape of tipbud.*—Rounded.

*Lenticels.*—Medium low density, approximately 6-8 per square centimeter, White RHS 155B in color, length 0.04 to 0.12 mm, diameter 0.04 to 0.08 mm.

Winter hardiness: Equivalent to 'Cripps Pink.'

Chilling requirement: 400 to 500 hours below 7° C.

Dormant one year old shoot: Pubescence medium.

*Size.*—Diameter 4 to 6 mm; Color medium brown; Internode length 49 to 56 mm.

Bloom period: Late; First bloom October 24 at Pemberton; Full bloom November 5 at Pemberton.

Leaves: Large, wide, long, oval, convex, pointed, medium thick, smooth.

*Leaf base shape.*—Ovate/cuneate.

*Length.*—84 to 111 mm.

*Width.*—45 to 56 mm.

*Thickness.*—0.1 mm to 0.2 mm.

*Upper leaf color.*—Yellow-Green RHS 147A.

*Lower leaf color.*—Yellow-Green, medium glossy on upper surface, green with weak pubescence on lower surface.

*Margin.*—Finely serrate, crenate.

*Petiole.*—Long, 26 to 41 mm, diameter 0.1 mm to 0.2 mm, medium slender, pubescent.

*Color.*—Yellow-Green RHS 144B.

*Stipule.*—Small, length 9 mm-15 mm, width 1.2 mm, texture smooth, sickle shape.

*Color.*—Yellow-Green RHS 147A.

*Central leaf vein.*—Color — Yellow-Green RHS 145D with pink tinge RHS N155B toward basal end.

Flowers:

*Buds.*—Unopened — Length 14 to 21 mm, diameter 8 to 12 mm; Red-Purple RHS 67A; Opened — Diameter 38 to 41 mm; Red-Purple RHS 69C; Quantity per spur 5.

*Size.*—Medium to Large, 48 mm to 52 mm in diameter; Depth 13 mm to 15 mm; Quantity per cluster 5.

*Shape.*—Ovoid to round.

*Color.*—Upper petal surface: Red-Purple RHS 67A; Lower petal surface: Red-Purple RHS 69C.

*Petals.*—5 petals per flower; ovate; Length 21 mm, width 14 mm; margin smooth to slightly ruffled.

*Pedicel.*—Length 34 mm; diameter 9 mm; Color Yellow-Green RHS 146D.

*Stamen.*—21 to 24 per flower; filaments length 5 mm to 9 mm, Color Greyed-Green RHS 192D.

*Pistil.*—Stigma — length 10 mm; Color Yellow RHS 1C; Styles — Length 9 mm to 10 mm, Yellow-Green RHS 144D.

*Sepals.*—5 per flower; length 8 mm, width 4 mm; Shape acuminate; Margin straight; Texture smooth; Upper surface Color Yellow-Green RHS 145B, Lower surface Color Yellow-Green RHS 145B; Arranged separately.

*Pollen.*—Yellow RHS 4C.

*Pollination requirements.*—These are no specific pollination requirements.

*Fragrance.*—Slight.

*Bloom period in Pemberton, Western Australia.*—

TABLE 1

The information below is for 2008 - 2009

| Variety | Green tip | Pink tip | Balloon | Full bloom |
|---|---|---|---|---|
| Fuji | 10th September | 15th September | 25th September | 5th October |
| 'PLMAS98' cv. | 15th September | 25th September | 30th September | 10th October |
| 'PLBARB1' cv. | 15th September | 25th September | 30th September | 10th October |
| 'Cripps Pink' cv. | 20th September | 30th September | 5th October | 18th October |

Fruit:

*Maturity when described.*—Eating ripe.

*Size.*—Large, uniform.

*Length.*—73 mm.

*Breadth.*—78 mm.

*Mean fruit weight.*—160 to 195 g.

*Form.*—Asymmetrical, ellipsoid-conical with a slight irregular surface; Medium distal crowns, rounded at base, sides slightly unbroken, unequal.

*Axis.*—Nonvertical.

*Cavity.*—Acute, deep 21 mm, medium width 34 mm, symmetrical, Color Yellow-Green RHS 145B, with very slight unbroken russet.

*Basin.*—Medium crown, ribbed, wide 32 mm, open, medium depth 12 mm.

*Markings.*—None.

*Sepals.*—Medium, touching.

*Stem.*—Medium length 22 mm, medium thickness 3 mm, not lipped.

*Calyx.*—Closed, V-shaped, medium width 20 mm and depth 11 mm to 12 mm.

*Calyx lobes.*—Reflexed and divergent.

*Pubescence.*—None.

Skin:

*Texture.*—Slightly bumpy, greasy.

*Bloom.*—Absent.

*Cracking tendency.*—Absent.

*Thickness.*—0.6 mm.

*Ground color.*—Yellow-green RHS 150B.

*Overcolor.*—Red-Purple RHS N57B.

*Percentage of overcolor.*—70% to 80%.

*Russet.*—None.

*Lenticels.*—Medium, 10 to 12 per square cm, numerous, roundish, diameter 0.9 mm, Color Green-White RHS 157A.

Flesh: Juicy, firm.

*Color.*—Yellow-White RHS 158C.

*Texture.*—Firm.

*Flavor.*—Rich, complex, sub acid to sweet.

*Aroma.*—Distinct, complex and highly aromatic.

*Brix.*—13-17.

*Browning of the flesh* (*one hour after being cut, with stainless steel knife*).—Nil.

*Quality.*—Best.

Core: Median.

*Bundle area.*—Medium small, symmetrical, Length 32 mm-34 mm, Width 29 mm-30 mm.

*Halves of area.*—Equal.

*Bundles.*—Inconspicuous.

*Core lines.*—Meeting, heart-shaped.

*Calyx tube.*—Funnel-form.

*Pubescence.*—None.

*Stem or funnel.*—Medium long.

*Depth of tube to shoulder.*—About 5 mm.

*Entire depth.*—About 12 mm.

*Styles.*—Some present, united at base.

*Carpels.*—Closed, axile, symmetrical, smooth, cordate form, emarginate at outer edge near tip.

Seeds:

*Quantity.*—One or two per cell, not tufted, acute at point, 8-9 mm long, 5 mm wide, obtuse.

*Color.*—Greyed-Orange RHS 177A.

Harvest date:

TABLE 2

Harvest dates in Pemberton, Western Australia 2008-2009

| Variety | Firstlick | Second pick | Final pick |
|---|---|---|---|
| Fuji | April 9 | | |
| 'PLMAS98' cv. | March 30 | | |
| 'PLBARB1' cv. | March 30 | | |
| 'Cripps Pink' cv. | May 1 | May 11 | May 28 |

Resistance to known diseases: None noted.

Keeping quality: Good. Fruit van be stored up to 6 months in cold storage (34° F.).

I claim:

1. A new and distinct apple tree substantially as described and illustrated herein.

* * * * *